United States Patent [19] [11] Patent Number: 4,985,463
Kreidl et al. [45] Date of Patent: Jan. 15, 1991

[54] AMINODIARYL SULFOXIDE DERIVATIVES, PROCESS FOR THEIR PREPARATION AND PHARMACEUTICAL AND PESTICIDAL COMPOSITIONS CONTAINING THEM

[75] Inventors: János Kreidl; Péter Turcsányi; Zsuzsanna Arcs née Trischler; Béla Stefkó; Judit M. Mészáros née Brill; Ida Deutsch née Juhász; Jenó Szilbereky; Eva Csizér; Szilárd Vezér, all of Budapest, Hungary

[73] Assignee: Richter Gedeon Vegyeszeti Gyar Rt, Budapest, Hungary

[21] Appl. No.: 706,707

[22] Filed: Feb. 28, 1985

[30] Foreign Application Priority Data

Feb. 29, 1984 [HU] Hungary ................ 815/84

[51] Int. Cl.$^5$ ........................................ A01N 33/02
[52] U.S. Cl. ........................................ 514/646; 71/3; 71/103; 564/430
[58] Field of Search ............... 564/430; 71/121, 103; 514/646

[56] References Cited

U.S. PATENT DOCUMENTS

| 3,050,440 | 8/1962 | Richter | 568/36 |
| 3,125,604 | 3/1964 | Robbins | 564/430 X |
| 3,186,904 | 6/1968 | Stevenson et al. | 514/503 X |
| 3,551,500 | 12/1970 | Model et al. | 564/430 X |
| 3,702,362 | 11/1972 | Shen et al. | 564/430 X |
| 3,798,258 | 3/1974 | Patchett et al. | 564/430 X |
| 3,852,289 | 12/1974 | Mylari et al. | 564/430 X |
| 3,900,473 | 8/1975 | Diel et al. | 564/430 X |
| 3,914,310 | 10/1975 | Frick et al. | 564/430 |
| 3,988,477 | 10/1976 | Karrer et al. | 569/430 X |
| 3,998,972 | 12/1976 | Farooq et al. | 564/430 X |
| 4,105,797 | 8/1978 | Schneider et al. | 564/430 X |
| 4,279,637 | 7/1981 | Wu | 564/430 X |
| 4,331,817 | 5/1982 | Throckmorton | 564/430 |
| 4,393,211 | 7/1983 | Tonne et al. | 546/153 |
| 4,457,875 | 7/1984 | Fournier et al. | 260/543 |

FOREIGN PATENT DOCUMENTS 130800 6/1945 Austria.
448151 4/1948 Canada.
282214 2/1915 Fed. Rep. of Germany ...... 564/430

OTHER PUBLICATIONS

Averkin et al., "Jour. Med. Chem.", vol. 18, pp. 1164–1166 (1975).
Houben-Weyl, "Methoden der Organischen Chemie", vol. 11/1, pp. 416–421 (1957).

Primary Examiner—Robert V. Hines
Attorney, Agent, or Firm—Herbert Dubno; Jonathan Myers

[57] ABSTRACT

An antifungal or anthelmintic method of treatment is disclosed which comprises the step of administering to a mammal in need of said treatment, a pharmaceutically effective amount of a compound of the Formula (I)

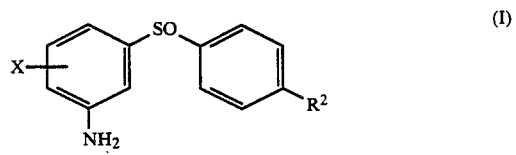

wherein
X is halogen, $C_1$ to $C_6$ alkoxy, or a group —$NRR^1$ in which R and $R^1$ are each hydrogen or $C_1$ to $C_6$ alkyl; and
$R^2$ is hydrogen, halogen, $C_1$ to $C_6$ alkyl, $C_1$ to $C_6$ alkoxy, phenyl, phenylthio, or phenyl or phenylthio substituted by at least one halogen or amino substituent; or a pharmaceutically acceptable acid addition salt thereof.

2 Claims, No Drawings

AMINODIARYL SULFOXIDE DERIVATIVES, PROCESS FOR THEIR PREPARATION AND PHARMACEUTICAL AND PESTICIDAL COMPOSITIONS CONTAINING THEM

The invention relates to a new process for the preparation of aminodiaryl sulfoxide derivatives of the formula (I),

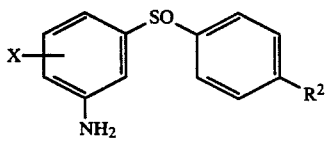

wherein
X is halogen, alkoxy having from 1 to 6 carbon atoms or a group $-N(R,R^1)$, in which R and $R^1$ are hydrogen or alkyl having from 1 to 6 carbon atoms,
$R^2$ is hydrogen, halogen, alkyl having from 1 to 6 carbon atoms, alkoxy having from 1 to 6 carbon atoms or phenyl or phenylthio both optionally substituted by one or more identical or different halogen(s) and/or amino group(s),
and acid addition salts thereof, by reducing a nitrodiaryl sulfoxide of the formula (II),

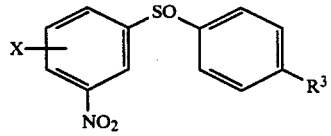

wherein X, R, $R^1$ are as defined above, and $R^3$ is hydrogen, halogen, alkyl or alkoxy both having 1 to 6 carbon atoms or phenyl or thiophenyl both optionally substituted by one or more identical or different halogens and/or nitro, with a sulfide of the formula (III),

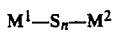

wherein
$M^1$ and $M^2$ are identical or different, and
$M^1$ is an alkali metal ion or ammonium ion,
$M^2$ is hydrogen, alkali metal ion or ammonium ion,
n is an integer between 1 and 9,
and, if desired, treating an aminodiaryl sulfoxide of the formula (I) obtained, in which X, R, $R^1$ and $R^2$ are as defined above, with and acid.

In the formula (I) X and $R^2$ as halogen represent fluroine, chlorine, bromine or iodine, preferably chlorine; while as an alkoxy having from 1 to 6 carbon atoms they stand for a straight-chained or branched alkoxy having from 1 to 6 carbon atoms, such as methoxy, ethoxy, n-propoxy, isopropoxy, n-butoxy, sec.-butoxy, tert.-butoxy, isobutoxy, n-pentoxy, isopentoxy, n-hexyloxy, isohexyloxy, etc., preferably methoxy.

In the definition of R, $R^1$ and $R^2$ the term "alkyl having from 1 to 6 carbon atoms" is used to refer to straight-chained or branched alkyl groups, such as e.g. methyl, ethyl, n-propyl, isopropyl, n-butyl, isobutyl, sec.-butyl, tert.butyl, n-pentyl, isopentyl, n-hexyl and isohexyl groups.

In the compounds of formula (III) $M^1$ and $M^2$ as an alkali metal ion for example represent a potassium or sodium ion.

Compounds of the formula (I) are pharmaceutically active, and are particularly useful in the veterinary therapy as anthelminitics; on the other hand, show valuable pesticidal, particularly insecticidal, acaricidal and especially fungicidal and herbicidal activity.

The invention therefore relates to pharmaceutical compositions comprising as active ingredient at least one compound of formula (I) or a physiologically acceptable salt thereof, in association with pharmaceutical carriers and/or excipients.

According to another aspect of the invention there are provided pesticidal compositions containing as active ingredient at least one compound of formula (I) or a salt thereof, in association with at least one conventional carrier and optionally further additives.

The compounds of the formula (I) are further valuable intermediates in the preparation of other, new and known bioactive aromatic sulfoxide derivatives, such as benzimidazole-and other substituted diaminosulfoxide derivatives having anthelmintic and fungicidal activity (see e.g. the Published German Patent Applications Nos. 2,406,584 and 2,739,215 and the United States Patent Specification No. 4,011,320). These compounds may for example be prepared by coupling the compounds according to the invention with a carbamic acid ester derivative.

The compounds of the formula (I), in which X is a group $-N(R,R^1)$ being attached to the phenyl ring in the para-position relative to the sulfoxide group, and R and $R^1$ both stand for hydrogen, $R^2$ stands for hydrogen or halogen or an alkyl or alkoxy group having from 1 to 6 carbon atoms, are known in the art, while the other compounds of formula (I) are new. For the known compounds, however, no biological activity has been reported so far.

The known compound of the formula (I), in which $R^2$ is hydrogen is e.g. disclosed in J. Med. Chem. 1975, (18), 1164. According to the prior art, this compound was for example prepared by reacting 5-chloro-2-nitroaniline with thiophenyl and oxidizing the phenyl-(3-amino-4-nitrophenyl) sulfide obtained with a peracid (see the above article) or, according to the Published German patent application No. 1,438,120, by reacting 5-chloro-2-nitroaniline with sodium benzenesulfinate, and subsequently subjecting the phenyl-(3-amino-4-nitro-phenyl) sulfoxide obtained by any of these procedures, (in which the nitro group is in para-position relative to the sulfoxide group, unlike in the instant compounds, in which the nitro group is in the meta-position) to catalytic hydrogenation, in the presence of a palladium-on-charcoal catalyst. The drawbacks of these processes are as follows:

The known processes involve a catalytic hydrogenation step. During this step, due to the desactivating effect of the sulfur atom having a free electrom pair, a large amount of noble metal catalyst is required. This results in substantial extra costs, even if the catalyst is regenerated and recycled most carefully, This, together with the expensive safety equipment to be used in catalytic hydrogenation processes, means that the synthesis cannot be carried out economically on an industrial scale. A further disadvantage is that during catalytic hydrogenation, at a given temperature and pressure, the sulfoxide compounds are reduced to sulfides and bis-nitrogen compounds are formed, and if in the formula (II) X stands for halogen, also dehalogenation may take place during the catalytic hydrogenation of nitroaryl compounds as a side-reaction. Therefore, the product obtained must be further purified.

A nitro group can generally be reduced into an amino group also with a chemical reducing agent. A well-known chemical reducing agent is sodium dithionite, but if this compound is used for the desired reduction, sulfonation takes place as a side-reaction, which decreases the yield of the reaction and results in a contaminated product. Other reducing agents, e.g. SnCl$_2$ would make the reaction too expensive, while the reduction with iron powder in the presence of a ferro-salt and an acid is very difficult to carry out on an industrial scale. The molecules which contain a nitro group in the para-position related to the sulfoxide group are very stable, therefore their nitrogen is rather resistant to chemical reducing agents, while under more aggressive conditions other side-reactions affecting the bonds of the sulfur atom take also place, which result in a lower yield and a contaminated product. Among the reductions known in the art there is no one which would relate to the reduction of compounds of the formula (II), in which the nitro group is in meta-position related to the sulfoxide group.

We have surprisingly found that the reduction of a meta-nitrophenyl sulfoxide of the formula (II) can be carried out with an excellent yield, without side-reaction, and yields the desired product in high purity, if as a chemical reducing agent a compound of the formula (III) is used during the reduction. Typical representatives of the compounds of formula (III) are alkali metal sulfides, ammonium sulfide, alkali metal bisulfides, alkali metal polysulfides, etc. The yield and the purity of the product are better than in the case of catalytic hydrogenation and the reaction conditions are very mild.

The process according to the invention is generally carried out in a (70:30)–(5:95) mixture of water and an aliphatic alcohol having from 1 to 6 carbon atoms, e.g. methanol, ethanol, n-propanol, isopropanol, n-butanol, sec.-butanol, tert.-butanol, etc. The reaction temperature and the reaction time depend on the starting materials employed. The reaction is preferably carried out between 60° C. and 100° C. in 0.5 to 6 hours.

The isolation of the product is carried out in a conventional manner, e.g. by diluting the reaction mixture with water, which results in the precipitation of the product in a pure form.

By the process according to the invention diaminodiaryl sulfoxides can be prepared with a better yield and in a better quality than by catalytic hydrogenation. In this manner the use of a large amount of noble metal catalyst (which is necessary in the catalytic hydrogenation due to the desactivating effect of sulfur) can be avoided, and the process can be carried out without any expensive safety apparatus. The reducing agents used in the process according to the invention are cheap, readily available commerical products. By this process more easily accessible starting materials can also be converted into the desired end products. The reduction is performed under mild conditions, i.e. under atmospheric pressure in a relatively short time. The process is practically free of corrosive side-effects and is easy to carry out even on industrial scale.

The nitrodiaryl sulfoxide starting materials of formula (II) may for example be prepared by reducing and subsequently halogenating an arylsulfonyl halide, treating the product obtained with a benzene derivative and, if desired, reacting the nitrodiaryl sulfoxide obtained with an amine or compound supplying an amine. Further details of this process are to be found in our copending patent application corresponding to our Hungarian patent application No. 813/84 (corresponding to our copending concurrently filed U.S. application Ser. No. 706,704 abandoned.

According to a still further aspect of the invention there are provided new compounds of the formula (I),

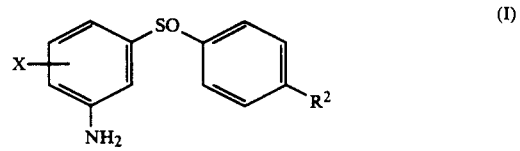

in which
X is halogen, alkoxy having from 1 to 6 carbon atoms or a group —N(R,R$^1$), wherein
R and R$^1$ are hydrogen or alkyl having from 1 to 6 carbon atoms,
R$^2$ is hydrogen, halogen, alkyl having from 1 to 6 carbon atoms, alkoxy having from 1 to 6 carbon atoms, or phenyl or phenylthio both optionally substituted by one or more, identical or different halogen(s) and/or nitro group(s), provided that if X stands for a group —N(R,R$^1$), in which R and R$^1$ both are hydrogen, and X is in para-position related to the sulfoxide group, then R$^2$ is other than hydrogen, halogen, alkyl having from 1 to 6 carbon atoms or alkoxy having from 1 to 6 carbon atoms, and acid addition salts thereof.

The compounds of formula (I) can be converted into their acid addition salts by reaction with suitable acids. Suitable acids include e.g. inorganic acids, such as hydrogen halides, e.g. hydrochloric acid, hydrogen bromide, sulfuric acid, phosphoric acid, perhalogenic acids, e.g. perchloric acid, etc., organic acids, such as formic acid, acetic acid, propionic acid, glycolic acid, maleic acid, hydroxymaleic acid, fumaric acid, succinic acid, tartaric acid, ascorbic acid, citric acid, malic acid, salicylic acid, lactic acid, cinnamic acid, benzoic acid, phenylacetic acid, p-aminobenzoic acid, p-hydroxybenzoic acid, p-aminosalicylic acid, etc., alkylsulfonic acids, such as methanesulfonic acid, ethanesulfonic acid, etc., cycloaliphatic sulfonic acids, such as cyclohexylsulfonic acid; arylsulfonic acids, such as p-toluenesulfonic acid, naphthylsulfonic acid, sulfanilic acid, etc.; amino acids, such as aspartic acid, glutamic acid, N-acetyl-aspartic acid, N-acetylglutamic acid, etc.

Salt formation can be carried out, for example, in an inert organic solvent, such as a C$_{1-6}$ aliphatic alcohol, by dissolving the compound of the formula (I) in the solvent and adding the selected acid or a solution thereof formed with the same solvent to the first solution until it becomes slightly acidic (pH 5 to 6). Thereafter the acid addition salt separates and can be removed from the reaction mixture e.g. by filtration.

The compounds of the formula (I) or the salts thereof, if desired, can be subjected to further purification e.g. recrystallization. The solvents used for recrystallization are selected depending on the solubility and crystallization properties of the compound to be crystallized.

The active compounds of the formula (I) may be formulated for therapeutic purposes. The invention therefore relates also to pharmaceutical compositions comprising as active ingredient at least one compound of formula (I) or a physiologically acceptable salt thereof, in association with pharmaceutical carriers and/or excipients. Carriers conventional for this purpose and suitable for parenteral or enteral administration as well as other additives may be used. As carriers solid or liquid compounds, for example water, gelatine, lactose, starch, pectin, magnesium stearate, stearic acid, talc, vegetable oils, such as peanut oil, olive oil, etc. can be used. The compounds can be formulated as conventional pharmaceutical formulations, for example in a solid (globular and angular pills, dragées, e.g. hard gelatine capsules) or liquid (injectable oily or aqueous solutions or suspensions) form. The quantity of the solid carrier can be varied within wide ranges, but preferably is between 25 mg. and 1 g. The compositions optionally contain also conventional pharmaceutical additives, such as preserving agents, wetting agents, salts for adjusting the osmotic pressure, buffers, flavoring and aroma substances.

The compositions according to the invention optionally contain the compounds of the formula (I) in association with other known active ingredients. The unit doses are selected depending on the route of administration. The pharmaceutical compositions are prepared by conventional techniques including sieving, mixing, granulation, pressing or dissolution of the active ingredients. The formulations obtained are then subjected to additional conventional treatments, such as sterilization.

For use as pesticides, the compounds of the formula (I) are formulated as conventional formulations, e.g. solutions, emulsions, soluble powders, suspensions, powder compositions, aerosol compositions, suspension and emulsion concentrates, powders for seed dressing. The compounds can be used for impregnating natural and synthetic materials, may be formulated as microcapsules, using polymeric substances and materials suitable for coating seeds, or can be converted into formulations supplied with a burnable filling, such as smoke patrons, boxes, spirals, and warm or cold fog compositions, which may be applied by ULV (ultra-low-volume) technique.

The pesticidal compositions can be prepared in a manner known per se, for example by admixing the active ingredients with carriers, i.e. liquid solvents, liquified gases under pressure and/or solid carriers. If desired, also surfactants, emulsifying and/or dispersing and/or foaming agents can be added to the system. If water is used as a carrier, as a co-solvent organic solvents may also be employed. The liquid solvents essentially include aromatic compounds such as xylene, toluene or alkylnaphthalenes; chlorinated aromatic or chlorinated aliphatic hydrocarbons such as chlorobenzene, chloroethylene or methylene chloride; aliphatic hydrocarbons such as cyclohexane or paraffines such as mineral oil fractions, as well as alcohols such as butanol or glycol and the ethers and esters thereof; ketones such as acetone, methyl ethyl ketone, methyl isobutyl ketone or cyclohexanone; strongly polar solvents such as dimethyl formamide, dimethyl sulfoxide and water. Under liquidified gaseous carriers for example aerosol propellants such as halogenated hydrocarbons, butane, propane, nitrogen and carbon dioxide are meant. As solid carriers for example natural fossil meals, e.g. caoline, clay earth, talc, chalkstone, quartz, attapulgite, montmorillonite or diatomaceous earth, and synthetic fossil meals such as highly dispersed silicic acid, alumina and silicates are employed. As carriers for granulates for example broken and fractionated natural rocks, e.g. calcite, marbel, pumice, sepiolite, dolomite, and granulates of inorganic and organic meals, as well as granulates prepared from organic materials such as sawdust, coconut shell, corn husk and tobacco stems can be used. As emulsifying agents and/or foaming agents non-ionic and anionic emulsifiers such as polyoxyethylene fatty acid ethers, polyoxyethylene fatty alcohol ethers, e.g. alkylarylpolyglycol ether, alkylsulfonates, alkylsulfates, arylsulfonates and protein hydrolysates, while as dispersing agents e.g. lignine, sulfite waste liquors and methyl cellulose may be employed.

The pesticidal compositions according to the invention may contain also adhesives such as carboxymethyl cellulose, natural and synthetic, powdery, granular or latex-like polymers, e.g. acacia gum, polyvinyl alcohol, polyvinyl acetate, etc.

The pesticidal compositions according to the invention may further contain various pigments such as inorganic pigments, e.g. iron oxide, titanium dioxide, ferrocyane blue and organic pigments, e.g. alizarine, azometal phthalocyanine pigments, as well as micronutrients, e.g. iron, manganese, boron, copper, cobalt, molybdenum and zinc salts.

The pesticidal compositions generally contain 0.1 to 95% by weight, preferably 0.5 to 90% by weight of active ingredient.

The active ingredients may be applied in the form of commercial formulations and/or ready-to-use formulations prepared therefrom.

The active ingredient concentration of the ready-to-use formulations prepared from the commercial pesticidal compositions may vary within wide limits, and generally is between 0.000 000 1 and 95% by weight, preferably 0.01 and 10% by weight.

The route of application always depends on the specific formulation used.

The invention is elucidated in detail by the aid of the following non-limiting Examples.

EXAMPLE 1

Phenyl-(3,4-diaminophenyl) sulfoxide

To a suspension of 20 g. (0.076 moles) of phenyl-(4-amino-3-nitrophenyl) sulfoxide in 80 ml. of methanol a solution of 22 g. (0.17 moles) of sodium sulfide of 60% purity in 25 ml of water is added in one hour under boiling. The reaction mixture is then refluxed for 3 hours.

The progress of the reaction is monitored by thin layer chromatography (5:1 mixture of benzene and methanol, Merck Kieselgel/60F$_{254}$ Alufoil, u.v. detection). Thereafter 1 g. of celite or 1 g. of activated carbon is added to the reaction mixture, which is then filtered while hot. The filtrate is slowly cooled to room temperature, under stirring. The precipitated substance is filtered off. The material remaining on the filter is washed base-free with water and dried at 50° to 60° C.

16 g. of greyish-beige phenyl-(3,4-diaminophenyl)-sulfoxide are obtained, melting at 149° to 150° C.

From the mother liquor about 20 ml. of solvent are distilled off in vacuo, the distillation residue is diluted with 30 ml. of water and the precipitate is filtered off. The product weighing 1.2 g. is recrystallized from 6 ml. of 60% methanol to yield a further 1 g. of the desired compound, which has the same melting point as the compound prepared in the previous step.

Total yield: 95% of theoretical

EXAMPLE 2

3,4-Diaminophenyl-4-methylphenyl sulfoxide

To a suspension of 21.2 g. (0.076 moles) of (4-amino-3-nitrophenyl)-4-methylphenyl sulfoxide in 80 ml. of methanol a solution of 22 g. (0.17 moles) of sodium sulfide of 60% purity in 25 ml. of water is added in one hour, under boiling. The reaction mixture is refluxed for 3 hours, and the progress of the reaction is monitored by thin layer chromatography. Thereafter 1 g. of celite is added to the reaction mixture, which is then filtered while hot. The filtrate is diluted with 50 ml. of water, and is slowly cooled to room temperature. The precipitate is filtered off, and the substance remaining on the filter is washed base-free with water. The product is then dried at 50° to 60° C. to yield 17 g. of the title compound, melting at 131° to 132° C. Yield: 91% of theoretical,

EXAMPLE 3

Phenyl-(3-amino-4-dimethylaminophenyl) sulfoxide

Following the procedure described in Example 2 but using as a starting material instead of (4-amino-3-nitrophenyl)-4-methylphenyl sulfoxide a corresponding amount of phenyl-(4-dimethylamino-3-nitrophenyl) sulfoxide, the title compound is obtained.

Melting point: 85° to 86° C.
Yield: 90% of theoretical.

EXAMPLE 4

(3,4-Diaminophenyl)-(4-chlorophenyl) sulfoxide

Following the procedure described in Example 2 but using as a starting material instead of (4-amino-3-nitrophenyl) -4-methylphenyl sulfoxide a corresponding amount of (4-amino-3-nitrophenyl)-4-chlorophenyl sulfoxide, the title compound is obtained.

Melting point: 152° to 153° C.
Yield: 92% of theoretical.

EXAMPLE 5

4-(3,4-Diaminophenylsulfinyl)-biphenyl

Following the procedure described in Example 2 but using as a starting material instead of (4-amino-3-nitrophenyl)-4-methylphenyl sulfoxide a corresponding amount of 4-(4-amino-3-nitrophenylsulfinyl)-biphenyl, the title compound is obtained.

Melting point: 199° to 201° C.
Yield: 95% of theoretical.

EXAMPLE 6

[4-(4-Chloro-3-aminophenylthio)-phenyl]-3,4-diaminophenyl sulfoxide

Following the procedure described in Example 2 but using as a starting material instead of (4-amino-3-nitrophenyl)-4-methylphenyl sulfoxide a corresponding amount of [4-(4-chloro-3-nitrophenylthio)-phenyl]-4-amino-3-nitrophenyl sulfoxide, the title compound is obtained.

EXAMPLE 7

Phenyl-(3-amino-4-chlorophenyl) sulfoxide

Following the procedure described in Example 2 but using as a starting material instead of (4-amino-3-nitrophenyl)-4-methylphenyl sulfoxide a corresponding amount of phenyl-(4-chloro-3-nitrophenyl) sulfoxide, the title compound is obtained.

Melting point: 89° to 90° C.
Yield: 90% of theoretical.

EXAMPLE 8

3,4-Diaminophenyl-4-methoxyphenyl sulfoxide

Following the procedure described in Example 2 but using as a starting material instead of (4-amino-3-nitrophenyl)-4-methylphenyl sulfoxide a corresponding amount of (4-amino-3-nitrophenyl)-4-methoxyphenyl sulfoxide, the title compound is obtained.

Melting point: 145° to 147° C.
Yield: 90%.

EXAMPLE 9

3,4-Diaminophenyl-4-fluorophenyl sulfoxide

Following the procedure described in Example 2 but using as a starting material instead of (4-amino-3-nitrophenyl)-4-methylphenyl sulfoxide a corresponding amount of (4-amino-3-nitrophenyl)-4-fluorophenyl sulfoxide, the title compound is obtained.

Melting point: 81° to 83° C.
Yield: 91%.

EXAMPLE 10

4-Bromophenyl-3,4-diaminophenyl sulfoxide

Following the procedure described in Example 2 but using as a starting material instead of (4-amino-3-nitrophenyl)-4-methylphenyl sulfoxide a corresponding amount of 4-bromophenyl-(4-amino-3-nitrophenyl) sulfoxide, the title compound is obtained.

EXAMPLE 11

(3-Amino-4-methoxyphenyl)-phenyl sulfoxide

Following the procedure described in Example 2 but using as a starting material instead of (4-amino-3-nitrophenyl)-4-methylphenyl sulfoxide a corresponding amount of (4-methoxy-3-nitrophenyl)-phenyl sulfoxide, the title compound is obtained.

Melting point: 113° to 115° C.
Yield: 89% of theoretical.

EXAMPLE 12

(3-Amino-4-ethylaminophenyl)-phenyl sulfoxide

Following the procedure described in Example 2 but using as a starting material instead of (4-amino-3-nitrophenyl)-4-methylphenyl sulfoxide a corresponding amount of (4-ethylamino-3-nitrophenyl)-phenyl sulfoxide, the title compound is obtained.

Melting point: 140° to 142° C.
Yield: 93% of theoretical.

EXAMPLE 13

1-(4-Bromophenyl)-4-(3,4-diaminophenylsulfinyl)-benzene

Following the procedure described in Example 2 but using as a starting material instead of (4-amino-3-nitrophenyl)-4-methylphenyl sulfoxide a corresponding amount of 1-(4-bromophenyl)-4-(4-amino-3-nitrophenylsulfinyl)-benzene, the title compound is obtained; M.P.=161°-164° C.

EXAMPLE 14

3,4-Diaminophenyl-4-methylthiophenyl sulfoxide

Following the procedure described in Example 2 but using as a starting material instead of (4-amino-3-nitrophenyl)-4-methylphenyl sulfoxide a corresponding amount of (4-amino-3-nitrophenyl)-4-methylthiophenyl sulfoxide, the title compound is obtained.

EXAMPLE 15

(3-Amino-4-chlorophenyl)-4-fluorophenyl sulfoxide

Following the procedure described in Example 2 but using as a starting material instead of (4-amino-3-nitrophenyl)-4-methylphenyl sulfoxide a corresponding amount of 4-fluorophenyl-(4-chloro-3-nitrophenyl) sulfoxide, the title compound is obtained.

Yield: 90%; M.P.=82°–85° C.

EXAMPLE 16

(3-Amino-4-chlorophenyl)-4-methylphenyl sulfoxide

Following the procedure described in Example 2 but using as a starting material instead of (4-amino-3-nitrophenyl)-4-methylphenyl sulfoxide a corresponding amount of (4-chloro-3-nitrophenyl)-4-methylphenyl sulfoxide, the title compound is obtained: M.P.=119°–121° C.

Yield: 88%; M.P. 119°–121° C.

EXAMPLE 17

(3-Amino-4-chlorophenyl)-4-bromophenyl sulfoxide

Following the procedure described in Example 2 but using as a starting material instead of (4-amino-3-nitrophenyl)-4-methylphenyl sulfoxide a corresponding amount of 4-bromophenyl-4-(4-chloro-3-nitrophenyl) sulfoxide, the title compound is obtained.

Yield: 87%; M.P.=119°–122° C.

EXAMPLE 18

(5-Amino-2-chlorophenyl)-phenyl sulfoxide

Following the procedure described in Example 2 but using as a starting material instead of (4-amino-3-nitrophenyl)-4-methylphenyl sulfoxide a corresponding amount of (2-chloro-5-nitrophenyl)-phenyl sulfoxide, the title compound is obtained.

Yield: 89%; M.P.=152°–155° C.

EXAMPLE 19

(5-Amino-2-chlorophenyl)-4-chlorophenyl sulfoxide

Following the procedure described in Example 2 but using as a starting material instead of (4-amino-3-nitrophenyl)-4-methylphenyl sulfoxide a corresponding amount of 4-chlorophenyl-(2-chloro-5-nitrophenyl) sulfoxide, the title compound is obtained.

Yield: 87%; M.P.=156°–159° C.

EXAMPLE 20

(3-Amino-4-chlorophenyl)-4-methoxyphenyl sulfoxide

Following the procedure described in Example 2 but using as a starting material instead of (4-amino-3-nitrophenyl)-4-methylphenyl sulfoxide a corresponding amount of (4-chloro-3-nitrophenyl)-4-methoxyphenyl sulfoxide, the title compound is obtained.

Yield: 86%; M.P.=103°–105° C.

EXAMPLE 21

4-(3-Amino-4-chlorophenylsulfinyl)-biphenyl

Following the procedure described in Example 2 but using as a starting material instead of (4-amino-3-nitrophenyl)-4-methylphenyl sulfoxide a corresponding amount of 4-(4-chloro-3-nitrophenylsulfinyl)-biphenyl, the title compound is obtained.

Yield: 85%; M.P.=134°–137° C.

EXAMPLE 22

1-(4-Bromophenyl)-4-(3-amino-4-chlorophenylsulfinyl)benzene

Following the procedure described in Example 2 but using as a starting material instead of (4-amino-3-nitrophenyl)-4-methylphenyl sulfoxide a corresponding amount of 1-(4-bromophenyl)-4-(4-chloro-3-nitrophenylsulfinyl)benzene, the title compound is obtained.

Yield: 88%.

We claim:

1. An antifungal or anthelmintic method of treatment which comprises the step of administering to a mammal in need of said treatment a pharmaceutically effective amount of the compound of the Formula (I)

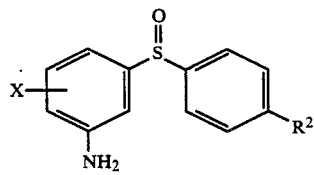

wherein
X is halogen, $C_1$ to $C_6$ alkoxy, or a group —$NRR^1$ in which R and $R^1$ are each hydrogen or $C_1$ to $C_6$ alkyl; and
$R^2$ is hydrogen, halogen, $C_1$ to $C_6$ alkyl, $C_1$ to $C_6$ alkoxy, phenyl, phenylthio, or phenyl or phenylthio substituted by at least one halogen, or amino substituent; or a pharmaceutically acceptable acid addition salt thereof.

2. A pesticidal method of treatment which comprises the step of administering to a plant site in need of said treatment a pesticidally effective amount of the compound of the Formula (I)

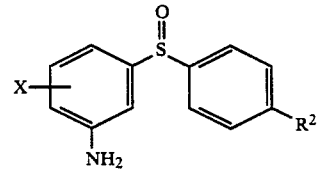

X is halogen, $C_1$ to $C_6$ alkoxy, or a group -$NRR^1$ in which R and $R^1$ are each hydrogen or $C_1$ to $C_6$ alkyl; and
$R^2$ is hydrogen, halogen, $C_1$ to $C_6$ alkyl, $C_1$ to $C_6$ alkoxy, phenyl, phenylthio, or phenyl or phenylthio substituted by at least one halogen, or amino substituent; or an acid addition salt thereof.

* * * * *